US008105689B2

(12) United States Patent
Craciun et al.

(10) Patent No.: US 8,105,689 B2
(45) Date of Patent: Jan. 31, 2012

(54) ADHESIVE, COATING OR FILM COMPOSITION APPLIED TO A SURFACE

(75) Inventors: Liliana Craciun, Carmel, NY (US); Orest Polishchuk, Bayonne, NJ (US); George William Schriver, Fort Lee, NJ (US); Gabriele Baisch, Binzen (DE); Reinhold Öhrlein, Rheinfelden-Herten (DE)

(73) Assignee: BASF SE, Ludwigshafen (DE)

( * ) Notice: Subject to any disclaimer, the term of this patent is extended or adjusted under 35 U.S.C. 154(b) by 1390 days.

(21) Appl. No.: 11/477,256

(22) Filed: Jun. 29, 2006

(65) Prior Publication Data

US 2007/0028805 A1    Feb. 8, 2007

Related U.S. Application Data

(60) Provisional application No. 60/697,790, filed on Jul. 8, 2005.

(51) Int. Cl.
*D02G 3/00* (2006.01)
(52) U.S. Cl. .. 428/375; 428/327; 428/356; 428/355 CN; 428/364; 428/379; 428/389; 428/407; 428/411.1; 428/432; 428/435; 428/441; 428/442; 428/458; 428/461; 428/463; 428/477.7; 428/500; 428/522; 522/1; 522/71; 522/81; 522/86; 522/152
(58) Field of Classification Search .................. 428/441, 428/442, 463, 327, 356, 355 CN, 364, 375, 428/379, 389, 407, 411.1, 432, 435, 458, 428/461, 477.7, 500, 522; 524/413, 431, 524/555; 522/1, 71, 81, 86, 152
See application file for complete search history.

(56) References Cited

U.S. PATENT DOCUMENTS

| | | | | |
|---|---|---|---|---|
| 2,934,555 | A | 4/1960 | O'Brien et al. | 260/461 |
| 3,030,347 | A | 4/1962 | O'Brien et al. | 260/86.1 |
| 3,351,617 | A | 11/1967 | Jaeger et al. | 260/78.5 |
| 3,823,124 | A | 7/1974 | Chang et al. | 260/89.7 |
| 3,884,628 | A | 5/1975 | Duffy et al. | 8/116 |
| 3,989,772 | A | 11/1976 | Hendricks et al. | 260/932 |
| 4,029,679 | A | 6/1977 | Kotzsch et al. | 260/348 |
| 4,526,728 | A | 7/1985 | Finke et al. | 260/502.5 |
| 4,650,591 | A | 3/1987 | Boothe et al. | 210/700 |
| 4,658,003 | A | 4/1987 | Schmidt et al. | 526/278 |
| 4,678,840 | A * | 7/1987 | Fong et al. | 525/340 |
| 4,738,870 | A | 4/1988 | Green et al. | 427/54.1 |
| 6,436,475 | B1 | 8/2002 | Adler et al. | 427/358 |
| 6,740,173 | B1 | 5/2004 | Pouyfaucon et al. | 148/250 |

FOREIGN PATENT DOCUMENTS

| | | |
|---|---|---|
| DE | 25 38 282 | 3/1977 |
| GB | 1 380 675 | 1/1975 |
| WO | 03/035013 | 5/2003 |

OTHER PUBLICATIONS

Bressy-Brondino, C. et al, Journal of Applied Polymer Science 2002, 83(11), 2277-2287.
Derwent Abstract No. 11143Y/07 English Language abstract of DE 25 38 282, (1977).

* cited by examiner

*Primary Examiner* — David W Wu
*Assistant Examiner* — Marie Reddick
(74) *Attorney, Agent, or Firm* — Shruti Costales

(57) ABSTRACT

The present invention relates to polymerizable N-substituted acrylamide phosphorus-containing monomers, organic polymers formed from the same. Incorporation of said monomers into adhesives, pigment dispersants, coatings or films for polar surfaces or particles gives improved adhesive, anti-corrosive, and flame retardant properties.

7 Claims, No Drawings

ADHESIVE, COATING OR FILM COMPOSITION APPLIED TO A SURFACE

This application claims the benefit of U.S. Provisional Ser. No. 60/697,790, filed Jul. 8, 2005 herein incorporated entirely by reference.

The present invention relates to polymerizable N-substituted acrylamide phosphorus-containing monomers and organic polymers formed from the same. Incorporation of said monomers into adhesives, pigment dispersants, coatings or films for polar surfaces or polar particles gives improved adhesive, anti-corrosive, and flame retardant properties.

BACKGROUND OF THE INVENTION

The use of phosphorus-containing materials as flame retardants, corrosion inhibitors, adhesion promoters, and scale inhibitors is well known. Conventional phosphorus-containing additives are non-polymerizable and suffer from several drawbacks such as migration and leaching, leading to modification of adhesive, coating or film properties over time. Commercially available phosphorus-containing monomers, such as vinylphosphonic acid and ethylphosphonic acid monovinyl ester exhibit a reduced tendency for polymerization and give polymers with low molecular weight.

Commercially available alkylphosphates containing (meth)acrylic functionality show reduced hydrolytic stability, as the phosphate or methacrylate ester bond can be cleaved in the presence of water. This reduces their storage stability and limits their applications.

(Meth)acrylic phosphonic acids and esters are known to be more hydrolytically stable than analogous phosphate acids and esters. These monomers are also known for their flame retardant activity, scale inhibiting activity and imparting adhesive properties in coatings.

For example, U.S. Pat. Nos. 3,030,347 and 2,934,555 teach dialkylphosphonoalkyl acrylate and methacrylate copolymers and methods for preparation. The compounds are used in leather or textile finishes for imparting flame retardancy.

U.S. Pat. No. 3,884,628 teaches N-phosphonomethylacrylamide as flame retardant for textiles.

U.S. Pat. No. 3,989,772 discloses N,N-bis-(phosphonomethyl)-acrylamides. The compounds are alleged to be suitable as flame proofing agents.

U.S. Pat. No. 4,526,728 discusses phosphonate monomers for dyeing auxiliaries and scale inhibitors.

U.S. Pat. No. 3,351,617 discloses a condensation product of methylolacrylamide and β-(dimethylphosphono)-propionamide and the use of the formed monomer as a flame retardant in fabric treatment.

U.S. Pat. No. 4,650,591 discloses acrylamido-2-methylpropanephosphonic acid as a corrosion inhibitor and its use as a scale inhibitor.

PCT application no. WO03/035013 discloses self-priming dental adhesive compositions containing phosphonic acid moieties. The invention alleges adhesion to enamel and/or dentin with a bond strength of at least 8 Mpa.

It is known to apply (meth)acrylic phosphonic acids and esters directly to a surface such as a metal to promote adhesion. In some cases the (meth)acrylic phosphonic acids and esters are polymerized directly onto a surface via radiation curing in the presence of other monomers.

For example, U.S. Pat. No. 4,029,679 discloses phosphonate monomers as a metal primer.

U.S. Pat. No. 6,740,173 discloses the use of phosphonate oligomer and phosphonate monomers (phosphonated methacrylates) in a composition for preventing metal corrosion with binder and metal reactive additives.

Bressy-Brondino, C. et al, Journal of Applied Polymer Science 2002, 83(11), 2277-2287, discloses blends of poly (vinylidene fluoride) and copolymers of methyl methacrylate and dimethyl 2-methylacryloyloxyethylphosphonate as a coating on steel.

U.S. Pat. No. 6,436,475 discloses a process for treating zinc, magnesium or aluminum wherein an organic compound with at least one phosphoric or phosphonic acid group is applied onto the metallic surface.

U.S. Pat. Nos. 4,738,870 and 4,658,003 disclose hydroxyphosphinylalkyl(meth)acrylate as adhesion promoting monomers.

There is still a need for hydrolytically stable phosphorus-containing monomers, which may be incorporated into adhesive, coating or film compositions either by polymerization into the polymeric component of the composition or as a polymerizable additive per se. The incorporated monomers of the invention remain surprisingly hydrolytically stable in water-borne formulations such as latex while still retaining their adhesive properties.

This invention makes available hydrolysis-stable phosphorus-containing (meth)acrylamide monomers. These monomers can be polymerized using conventional radical initiators, photoinitiators and/or thermal initiators to give polymers with improved adhesive, flame retardant, scale inhibition, dispersing and/or anti-corrosive properties suitable for use in adhesives, paints and coatings, or plastics.

SUMMARY OF THE INVENTION

The invention encompasses an adhesive, coating or film composition comprising a polymer formed from at least one N-substituted acrylamide monomer, which monomer comprises at least one phosphonic or phosphinic acid or ester moiety.

The N-substituted acrylamide monomer may be polymerized, optionally with other polymerizable monomers, and incorporated into the coating, film or adhesive before being applied to a surface. It may also be polymerized on a surface directly by such means as radiation or thermal curing.

The polymerizable N-substituted acrylamide monomer(s) may be for example represented by a formulae (I) or (II) or (III) or (IV)

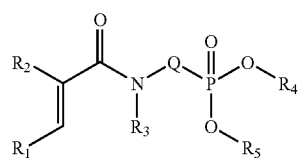

(I)

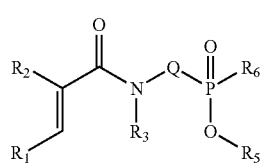

(II)

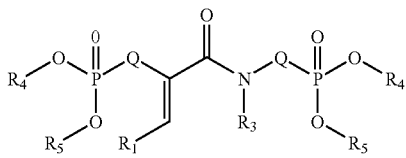

(III)

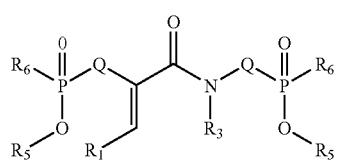

(IV)

wherein
Q is at least a divalent linking radical selected from the group consisting of one or more of a $C_1$-$C_{18}$ alkylene, $C_6$-$C_{12}$ arylene, or aralkylene;
wherein the linking group is unsubstituted or substituted by one or more $C_1$-$C_4$ alkyl, $C_1$-$C_4$ haloalkyl, halogen, —P(O)(OR$_4$)(OR$_5$), -Q'-P(O)(OR$_4$)(OR$_5$), —P(O)(OR$_4$)(R$_6$), -Q'-P(O)(OR$_4$)(R$_6$), hydroxy or $C_1$-$C_4$ alkoxy;
or
Q is a $C_2$-$C_{12}$ alkylene interrupted by one or more —O—, —S—, —NR$_4$—, —O(CO)—, —S(CO)—, —OC(O)O—, —NR$_4$—C(O)—O—, —C(O)— or —NR$_4$(CO)—;
$R_1$ and $R_2$ are independently hydrogen, branched or unbranched $C_1$-$C_4$ alkyl;
$R_3$ is hydrogen or $C_1$-$C_4$ alkyl, -Q'-P(O)(OR$_4$)(OR$_5$) or -Q"-P(O)(OR$_4$)(R$_6$);
Q' and Q" are the same or different and are at least a divalent radical selected from the group consisting of one or more of a $C_1$-$C_{18}$ alkylene, $C_6$-$C_{12}$ arylene, xylylene or aralkylene;
wherein the linking group is unsubstituted or substituted by one or more $C_1$-$C_4$ alkyl, $C_1$-$C_4$ haloalkyl, halogen, —P(O)(OR$_4$)(OR$_5$), —P(O)(OR$_4$)(R$_6$) hydroxy or $C_1$-$C_4$ alkoxy;
or
Q' and Q" are a $C_2$-$C_{12}$ alkylene interrupted by one or more —O—, —S—, —NR$_4$—, —O(CO)—, —S(CO)—, —OC(O)O—, —NR$_4$—C(O)—O—, —C(O)— or —NR$_4$(CO)—;
$R_4$ and $R_5$ are independently H, $C_1$-$C_4$ alkyl wherein the $C_1$-$C_4$ alkyl is branched or unbranched, unsubstituted or substituted by $C_1$-$C_4$ alkyl, $C_6$-$C_{12}$ aryl or halogen
and
$R_6$ is hydrogen, branched or unbranched $C_1$-$C_8$ alkyl, aryl or aralkyl, wherein the alkyl, aryl or aralkyl is unsubstituted or substituted by one or more $C_1$-$C_4$ alkyl, $C_1$-$C_4$ haloalkyl or halogen.

At least one of $R_4$ or $R_5$ is preferably hydrogen.

$C_1$-$C_{18}$ alkylene is linear or branched and is, for example, $C_1$-$C_8$, $C_1$-$C_6$ or $C_1$-$C_4$ alkylene. Examples are methylene, ethylene, propylene, butylene, pentylene, hexylene, heptylene, octylene, nonylene, decylene, undecylene and dodecylene. Preferred is $C_1$-$C_8$ alkylene, especially $C_1$-$C_6$ alkylene, preferably $C_1$-$C_4$ alkylene, such as methylene or butylene.

$C_6$-$C_{12}$ arylene is, for example, o-, m- or p-phenylene, 1,4-naphthylene or 4,4'-diphenylene. Other examples of arylene are phenylene, naphthylene, biphenylene, biphenylene ether and anthracenylene.

$C_1$-$C_4$ alkoxy is, for example, methoxy, ethoxy, propoxy and butoxy, it being possible for the alkyl radicals in alkoxy groups having more than two carbon atoms also to be branched.

The term "aralkylene group" is for example benzylene in which both the aliphatic hydrocarbon group and aromatic hydrocarbon group may be unsubstituted or substituted. The aralkylene may be unsubstituted or substituted by $C_1$-$C_4$ alkyl or $C_1$-$C_4$ alkoxy, or polyoxyalkylene having 2 to 12 oxyalkylene units and 2 to 6 C atoms in the alkylene.

$C_2$-$C_{12}$ alkylene interrupted by one or more —O—, —S—, —NR$_4$—, —O(CO)—, —S(CO)—, —OC(O)O—, —NR$_4$—C(O)—O—, —C(O)— or —NR$_4$(CO)— groups may be for example interrupted once or several times by —O—. For example, it may be interrupted from one to five times, for example from one to three times or once or twice, by non-successive —O—. Accordingly, resulting structural units are for example: —CH$_2$—O(CH$_2$)$_2$O—CH$_2$—, —CH$_2$—O—CH$_2$—, and —CH$_2$CH$_2$—O—CH$_2$CH$_2$—.

As the monomer is a phosphonic or phosphinic ester or acid, Q must at least contain a carbon atom directly bound to the phosphorus in formulae (I-IV). There is also no heteroatom directly connected to the amide of the (meth)acrylic acid portion of formulae (I-IV). By heteroatom it is meant non-hydrogen atoms other than carbon. For example, oxygen, sulfur and nitrogen are heteroatoms.

The term "halogen" means fluorine, chlorine, bromine and iodine.

$C_1$-$C_4$ alkyl is typically linear or branched. For example, $C_1$-$C_4$ alkyl may be methyl, ethyl, n-propyl, isopropyl, n-butyl, sec-butyl, isobutyl or tert-butyl.

$C_1$-$C_4$ haloalkyl are $C_1$-$C_4$-alkyl mono- or poly-substituted by halogen, for example, from one to three or one or two halogen substituents at the alkyl radical. Examples are chloromethyl, trichloromethyl, difluoromethyl, trifluoromethyl or 2-bromopropyl.

The terms "haloalkyl (or halogen-substituted alkyl) mean groups given by partially or wholly substituting the above-mentioned alkyl group with halogen, such as trifluoromethyl etc.

$C_1$-$C_8$ alkyl are branched or unbranched radicals, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, or n-octyl.

Examples of $C_1$-$C_4$ alkoxy are methoxy, ethoxy, n-propoxy, isopropoxy, n-butoxy, sec-butoxy, isobutoxy or tert-butoxy.

Compounds of formulae (II), (III) and (IV) are believed to be novel with the proviso that if the compound is of formula (II), $R_6$ is hydrogen.

It is preferably that at least one of $R_4$ and/or $R_5$ are hydrogen in formulae (I) and (III).

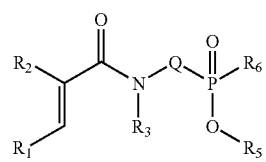

(II)

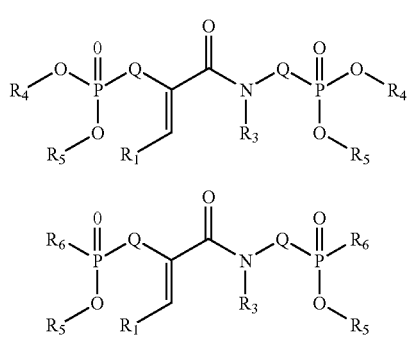

R$_5$ of formulae (II) and (IV) is for example hydrogen.

The phosphorus containing monomer may be incorporated into the coating or film by polymerization of the monomer with other ethylenically unsaturated monomers to form a polymer, which is then incorporated into the adhesive, coating or film. The phosphorus containing monomer may be used as a primer applied to the surface upon which the coating is to be applied. The monomer may also be grafted onto a polymer and the resulting grafted polymer may be incorporated into the adhesive, coating or film. The monomer may also be incorporated into a radiation curable adhesive, coating or film. In this case, the monomer can be applied to surface and copolymerized via radiation in the presence of a free radical initiator by ultra-violet (UV) cure or by electron beam (EB) cure, to produce phosphorus-containing polymers with strong adhesion to the polar surface.

It has been discovered that these acrylamide phosphonic or phosphinic acids or esters, improve the adhesion of organic substances to polar surfaces or polar particles. The adhesion improving function can be accomplished by treating the surface with the acrylamide phosphonic or phosphinic acid or esters directly or the phosphonic or phosphinic monomers may be dissolved in a solvent before treatment of the surface or particles. The acrylamide phosphonic or phosphinic monomer may also be incorporated in a conventional protective coating of a synthetic or natural organic material, such as a paint, lacquer, resin, plastic or rubber by polymerizing into one or more of the polymeric components of the adhesive, coating or film. The formed polymers from the acrylamide phosphonic or phosphinic acids or esters may also be used as dispersing agents for pigment particles within the adhesive, coating or film. The pigment dispersing properties of the formed polymer are improved, especially when the pigment is polar or metal based.

Not only is the adhesion of the coating improved but the hydrolytic stability of the coating is also improved relative to phosphate esters thereby allowing incorporation of the acrylamide phosphonic or phosphinic monomer or polymers derived from the same into water-borne coatings and latexes.

Thus the invention encompasses a method for improving the adhesion of a coating, adhesive or film to a surface, wherein the acrylamide phosphonic or phosphinic acids or esters are incorporated into the coating, film or adhesive composition and applied to said surface. Polymerization of the coating, dispersant, film or adhesive composition may be effected before or after application to the substrate.

Furthermore, the invention may also encompass a method of improving the adhesion of a coating, adhesive or film to a surface, wherein the acrylamide phosphonic or phosphinic acids or esters are applied to the surface before application of the coating or film to said surface.

For example, acrylamide phosphonic or phosphinic acids or esters are used to treat a metal substrate, then applying a coating, adhesive or film to the treated metal substrate and effecting polymerization of the coating, dispersant, adhesive or film containing the acrylamide phosphonic or phoshinic acids or esters.

DETAILED DESCRIPTION OF THE INVENTION

Alkylphosphonic acids are of great industrial importance and are widely employed, themselves or in the form of their salts, esters and anhydrides, in a variety of areas of application such as: scale inhibition or water softening, ore flotation, flocculation, heavy metal complexation, dispersants, flame retardants, pharmaceuticals, and pesticides.

The present invention is concerned with polymerizable N-substituted acrylamide monomers, which contain at least one phosphonic or phosphinic acid or ester moiety. These phosphorus containing amides are more hydrolytically stable than their phosphate analogs, easily polymerizable under conventional radical polymerization either alone or mixed with other polymerizable co-monomers, are compatible with many organic matrixes, and give materials with improved properties, e.g. adhesion, flame retardancy, anti-corrosion, dispersibility.

Once polymerized and incorporated into a polymer, the formed polymer per se will continue to provide improved adhesion to the substrate while retaining hydrolytic stability.

In particular, the polymerizable N-substituted acrylamide monomers may be incorporated into a coating, dispersant, film or adhesive.

Examples of coating materials are lacquers, paints or varnishes. These always contain an organic film-forming binder in addition to other, optional components. The binder may incorporate the polymerizable N-substituted acrylamide monomers.

Preferred organic film-forming binders are epoxy resins, polyurethane resins, amino resins, acrylic resins, acrylic copolymer resins, polyvinyl resins, phenolic resins, styrene/butadiene copolymer resins, vinyl/acrylic copolymer resins, polyester resins or alkyd resins, or a mixture of two or more of these resins, or an aqueous basic or acidic dispersion of these resins or mixtures of these resins, or an aqueous emulsion of these resins or mixtures of these resins.

Of particular interest are organic film-forming binders for aqueous coating compositions, such as, for example, alkyd resins; acrylic resins, two-component epoxy resins; polyurethane resins; polyester resins, which are usually saturated; water-dilutable phenolic resins or derived dispersions; water-dilutable urea resins; resins based on vinyl/acrylic copolymers; and hybrid systems based on, for example, epoxy acrylates.

The acrylic resins can be pure acrylic resins, epoxy acrylate hybrid systems, acrylic acid or acrylic ester copolymers, combinations with vinyl resins, or copolymers with vinyl monomers such as vinyl acetate, styrene or butadiene. These systems can be air-drying systems and stoving systems.

For example, the phosphonate or phosphinic monomers may be polymerized with one or more unsaturated compounds, which may contain one or more ethylenically unsaturated double bonds. They may be low molecular weight (monomeric) or higher molecular weight (oligomeric). Examples of monomers having a double bond are alkyl and hydroxyalkyl acrylates and methacrylates, e.g. methyl, ethyl, butyl, 2-ethylhexyl and 2-hydroxyethyl acrylate, isobornyl acrylate and methyl and ethyl methacrylate. Also of interest are silicone acrylates. Further examples are acrylonitrile, acrylamide, methacrylamide, N-substituted (meth)acrylamides, vinyl esters, such as vinyl acetate, vinyl ethers, such as isobutyl vinyl ether, styrene, alkyl- and halo-styrenes, N-vinylpyrrolidone, vinyl chloride and vinylidene chloride.

Examples of monomers having a plurality of double bonds are ethylene glycol diacrylate, propylene glycol diacrylate, neopentyl glycol diacrylate, hexamethylene glycol diacrylate and bisphenol A diacrylate, 4,4'-bis(2-acryloyloxyethoxy) diphenylpropane, trimethylolpropane triacrylate, pentaerythritol triacrylate and pentaerythritol tetraacrylate, vinyl acrylate, divinylbenzene, divinyl succinate, diallyl phthalate, triallyl phosphate, triallyl isocyanurate, ethylene glycol dimethacrylate, tris(hydroxyethyl)isocyanurate triacrylate and tris(2-acryloylethyl)isocyanurate or similar methacrylate analogues.

Especially suitable are, for example, esters of ethylenically unsaturated carboxylic acids and polyols or polyepoxides, and polymers having ethylenically unsaturated groups in the chain or in side groups, e.g. unsaturated polyesters, polyamides and polyurethanes and copolymers thereof, alkyd resins, polybutadiene and butadiene copolymers, polyisoprene and isoprene copolymers, polymers and copolymers having (meth)acrylic groups in side chains, and also mixtures of one or more such polymers.

Examples of unsaturated carboxylic acids are acrylic acid, methacrylic acid, maleic acid, crotonic acid, itaconic acid, cinnamic acid and unsaturated fatty acids such as linoleic acid or oleic acid. Acrylic and methacrylic acid are preferred.

The phosphonate or phosphinic monomers may be incorporated into adhesives. For example incorporation of the phosphonate or phosphinic monomers into reactive acrylic adhesives is advantageous. Specifically, structural adhesive systems such as anaerobic and aerobic acrylic are envisioned.

Anaerobic adhesives are well known in the art and comprise mixtures of acrylic esters that remain liquid when exposed to air but harden when confined between metal surfaces. These adhesives may be used for example in locking threaded fasteners. The phosphonate or phosphonic monomers of the invention are particularly effective in this application, especially when the fastener surfaces are metal. While not being limited by theory, it is believed that the phosphonate or phosphinic monomers penetrate the metal fasteners via chelation thus partially dissolving the metal and improving adhesion between the threaded surfaces of the fasteners.

The formulations for these anaerobic adhesives contain monomers such as (meth)acrylate esters, (meth)acrylic acids and other vinyl polymerizable monomers.

The initiators or cure inducing compounds for anaerobic adhesives are primarily hydroperoxides. The inventive compositions may also include other conventional components, such as free radical initiators, other free radical co-accelerators, inhibitors of free radical generation, as well as metal catalysts, such as iron and copper.

Such hydroperoxide compounds are typically employed in the present invention in the range of from about 0.1 to about 10 percent by weight, based on the total weight of the composition, with about 1 to about 5 percent by weight being desirable.

Anaerobic adhesives may be further formulated with accelerators such as saccharin and aromatic amines.

Inhibitors such as hydroquinone, p-methoxyphenol and chelants are incorporated in the liquid anaerobic adhesive to prevent premature polymerization during shipping and storing.

Thus an anaerobic curable composition, comprising: (a) at least one N-substituted acrylamide monomer, which monomer comprises at least one phosphonic or phosphinic acid or ester moiety component or components; and (b) an anaerobic cure-inducing composition is envisioned.

Additionally encompassed by the invention is a process for preparing a reaction product from an anaerobic curable composition, comprising the steps of: apply an anaerobic curable composition according to the invention, to a desired substrate surface and exposing the composition to an anaerobic environment for a time sufficient to cure the composition.

Of course, the anaerobic curable composition of the invention also provides for a bond formed between two mated substrates with the inventive composition.

Aerobic adhesives are designed to cure rapidly and form tough bonds with structural strength. They may be used to provide highly adhesive sealants and coatings. Curing of the monomer formulations may be implemented by chemical, heat and ultraviolet light.

Therefore, it is the object of the present invention to provide an aerobically curing adhesive composition which rapidly forms a high-strength polymer resistant to heat, aging and moisture and which is useful for bonding a wide variety of similar materials and different materials (composites).

Thus aerobically curing compositions comprising free-radical polymerizable compounds, an initiator, and optionally conventional additives, characterized in that said composition contains as said free-radical polymerizable compounds (a) at least one N-substituted acrylamide monomer, which monomer comprises at least one phosphonic or phosphinic acid or ester moiety component or components is envisioned.

The phosphonate or phosphinic monomers may be polymerized by conventional means such as radiation, thermal or redox curing with other vinyl monomers to form coatings, films or adhesives.

Radiation for the purposes of the invention includes ultraviolet, visible and infra-red light as well as electronic beam initiation.

To achieve UV or visible cure, specific photoinitiators are added to the formulation of monomers. The photoinitiators form free radicals upon exposure to UV or visible light and cause the blend of monomer, oligomers and unsaturated components to cure.

Photoinitiators are well known in the art and include for example, benzophenone, benzophenone derivatives, acetophenone, acetophenone derivatives, for example alpha.-hydroxycycloalkyl phenyl ketones or 2-hydroxy-2-methyl-1-phenyl-propanone, dialkoxyacetophenones, .alpha.-hydroxy- or .alpha.-aminoacetophenones, e.g. (4-methylthiobenzoyl)-1-methyl-1-morpholinoethane, (4-morpholinobenzoyl)-1-benzyl-1-dimethylaminopropane, 4-aroyl-1,3-dioxolanes, benzoin alkyl ethers and benzil ketals, e.g. dimethyl benzil ketal, phenylglyoxalic esters and derivatives thereof, dimeric phenylglyoxalic esters, monoacyl phosphine oxides, e.g. (2,4,6-trimethylbenzoyl)diphenylphosphine oxide, bisacylphosphine oxides, bis(2,6-dimethoxy-benzoyl)-(2,4,4-trimethyl-pentyl)phosphine oxide, bis(2,4,6-trimethylbenzoyl)-phenylphosphine oxide, bis(2,4,6-trimethylbenzoyl)-2,4-dipentoxyphenylphosphine oxide, trisacylphosphine oxides, ferrocenium compounds, or titanocenes, e.g. bis(cyclopentadienyl)-bis(2,6-difluoro-3-pyrryl-phenyl)titanium.

The substrate may be inorganic or organic and can be in any solid form. Preferably, the substrate is in the form of a powder or particles, fiber, film or three-dimensional object.

The substrate may be inorganic or organic. For example the substrate may be thermoplastic, metal oxide, glass, ceramic, metal or metal alloy.

For example the substrate may be a metal such as steel, aluminum, copper, silver, zinc, titanium or gold.

The surface of the substrate is preferably polar. Examples of polar surfaces are metallic pigment particles, metal, glass or ceramic fibers, sheet metals such as steel, aluminum and metal alloys The substrate is typically not a textile, unless the textile is formed from metallic, glass or ceramic fibers.

Incorporation of the phosphonic or phosphinic acrylamide monomers of the invention into polymeric dispersants are especially advantageous when used to disperse metallic pigments.

Examples of metallic pigments are for example titanium dioxide, micronized titanium dioxide, iron oxide pigments, and metal complexes of phthalocyanine pigments. Special effect or interference pigments are of interest. These may be made from aluminum, copper, glass or mica and further coated with thin layers of refractive materials. Examples of interference pigments may be titanium dioxide coated aluminum, coated mica, and coated iron oxide in flake form.

The phosphonic or phosphinic moiety of the polymer, may chelate with the metallic pigments and prevent the metallic pigments from agglomerating, thus functioning as a highly efficient dispersant.

The polymerizable N-substituted acrylamide monomer(s) may be for example represented by the formulae (I), (II), (III) or (IV)

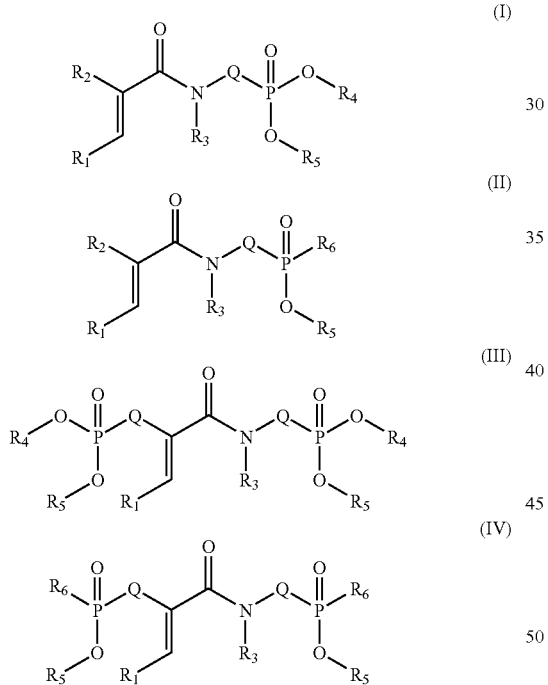

wherein
Q is at least a divalent linking radical selected from the group consisting of one or more of a $C_1$-$C_{18}$ alkylene, $C_6$-$C_{12}$ arylene, arylene, or aralkylene;
wherein the linking group is unsubstituted or substituted by one or more $C_1$-$C_4$ alkyl, $C_1$-$C_4$ haloalkyl, halogen, —P(O)(OR$_4$)(OR$_5$), -Q'-P(O)(OR$_4$)(OR$_5$), —P(O)(OR$_4$)(R$_6$), -Q'-P(O)(OR$_4$)(R$_6$), hydroxy or $C_1$-$C_4$ alkoxy;
or
Q is a $C_2$-$C_{12}$ alkylene interrupted by one or more —O—, —S—, —NR$_4$—, —O(CO)—, —S(CO)—, —OC(O)O—, —NR$_4$—C(O)—O—, —C(O)— or —NR$_4$(CO)—;

$R_1$ and $R_2$ are independently hydrogen, branched or unbranched $C_1$-$C_4$ alkyl;
$R_3$ is hydrogen or $C_1$-$C_4$ alkyl, -Q"-P(O)(OR$_4$)(OR$_5$) or -Q"-P(O)(OR$_4$)(R$_6$);
Q' and Q" are the same or different and are at least a divalent radical selected from the group consisting of one or more of a $C_1$-$C_{18}$ alkylene, $C_6$-$C_{12}$ arylene, or aralkylene;
wherein the linking group is unsubstituted or substituted by one or more $C_1$-$C_4$ alkyl, $C_1$-$C_4$ haloalkyl, halogen, —P(O)(OR$_4$)(OR$_5$), —P(O)(OR$_4$)(R$_6$) hydroxy or $C_1$-$C_4$ alkoxy;
or
Q' and Q" are $C_2$-$C_{12}$ alkylene interrupted by one or more —O—, —S—, —NR$_4$—, —O(CO)—, —S(CO)—, —OC(O)O—, —NR$_4$—C(O)—O—, —C(O)— or —NR$_4$(CO)—;
$R_4$ and $R_5$ are independently H, $C_1$-$C_4$ alkyl wherein the $C_1$-$C_4$ alkyl is branched or unbranched, unsubstituted or substituted by $C_1$-$C_4$ alkyl, $C_6$-$C_{12}$ aryl or halogen
and
$R_6$ is branched or unbranched $C_1$-$C_8$ alkyl, aryl, aralkyl, is unsubstituted or substituted by one or more $C_1$-$C_4$ alkyl, $C_1$-$C_4$ haloalkyl or halogen.
Preferably, at least one $R_4$ and/or $R_5$ are hydrogen.
By divalent radical it is meant that the linking group Q is covalently bound to at least the phosphorus and the amide of the acrylamide.
Some representative examples of formula (I) may be

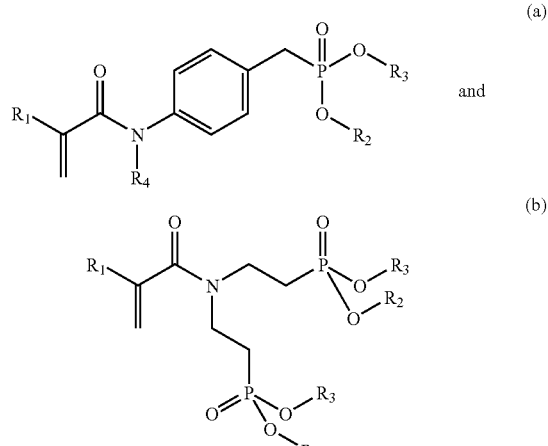

wherein $R_1$ is H or $C_1$-$C_4$ alkyl;
$R_2$ and $R_3$ are H or $C_1$-$C_4$ alkyl and the $C_1$-$C_4$ alkyl are unsubstituted or substituted with one of more halogens;
$R_4$ is H or $C_1$-$C_4$ alkyl.
Preferably at least one of $R_2$ or $R_3$ is hydrogen.
The phosphonic or phosphinic acrylamides compositions of the invention allow easy access to organic polymers with improved anti-corrosive and flame retardant properties, and in particular enhanced adhesion.

When the phosphonic or phosphinic acryamide compositions are used as flame retardants, they are normally at least about 10 to about 50 weight percent of the coating, adhesive, dispersant or film based on total solids. In order to obtain significant flame retardant property, relatively high amounts of phosphorus must be incorporated into a coating, film, dispersant or adhesive.

The phosphonic aor phosphinic acrylamides structural adhesives compositions of the invention do not encompass dental adhesives, especially wherein dentine enamel is the substrate or one of the substrates.

Effective concentrations of the phosphonic or phosphinic acrylamides for improving anti-corrosive, dispersant properties and adhesion properties of a coating, film, dispersant or adhesive may range from about 0.05 weight percent to about 10 weight percent, preferably, about 0.1 to about 5 weight percent and especially about 0.1 weight percent to about 3 weight percent, wherein the weight percent is based on the total dry weight of the coating, dispersant, film or adhesive. For example, about 0.05 to about 2 weight percent, about 0.05 weight percent to about 1 weight percent, about 0.2 weight percent to about 7 weight percent are envisioned. It is quite surprising that such low weight % levels of phosphonic or phosphinic acrylamides monomer incorporation improves the adhesion properties of the coating, dispersant, film or structural adhesive.

It is well known that adhesives show marked loss of bond strength in water. Thus the incorporation of the monomers of the invention into adhesive compositions is especially advantageous to preserving bond strength between surfaces. As little as about 0.05 weight percent imparts adhesion promotion and improved hydrolytic stability of the adhesive, coating or film.

The improved hydrolytic stability of (meth)acrylamide phosphonic or phosphinic acid or esters allows their use in aqueous media with applications as diverse as pigment dispersants or paint binders for metals. Particularly important is their use in the manufacture of latexes and water-borne systems where the monomers or formed polymers confer adhesion to metals and anti-corrosion properties. Thus for example formulation of a dispersant incorporating the phosphonic or phosphinic acrylamides provides two advantages to a coating, adhesive or film composition. The dispersant functions as an effective dispersant, preventing agglomeration of metal pigments such as TIO2 and improves adhesion to a polar substrate such as metal.

Acidic homopolymers and the copolymers (such as Dispex N40 and Dispex G40) which have been commercially used extensively as pigment dispersants give many satisfactory properties to the final film, a significant problem is that the final film often has inadequate resistance to water. As a result, the paint film is not as resistant to scrubbing with water as would be desirable.

The invention includes a dispersant co-polymer comprising, stable pigment dispersions formed using it as the sole or main dispersant and suitable for blending into emulsion paints, and emulsion paints formed using the pigment. The invention also includes the use of defined dispersant as a pigment dispersant in an emulsion paint which is to have improved water resistance, and the use of the emulsion paint for forming coatings having improved water resistance.

The pigment dispersant is a co-polymer formed from (a) at least one N-substituted acrylamide monomer, which monomer comprises at least one phosphonic or phosphinic acid or ester moiety component or components.

The copolymer is a suitable low molecular weight such that it functions as an effective dispersant and so the molecular weight is generally below about 100,000, preferably below about 70,000. It normally should be at least 2,500 and often at least 10,000. Preferred copolymers have a molecular weight in the range 20,000 to 60,000, preferably about 25,000 to about 50,000.

In this specification, all molecular weights are the Molecular Weight Average (Mw) values obtained by size exclusion chromatography using a set of Toso Haas PWXL columns (G4000+G3000+guard) and sodium polyacrylate standards and sodium acrylate monomer standards. Polystyrene standards may be used depending upon on whether the polymer is or not water-soluble.

The copolymer is generally made by solution polymerization in solvent in the presence of an appropriate initiator such as ammonium persulphate, in a manner conventional for the manufacture of low molecular weight polycarboxylic dispersants. The polymerization conveniently preferably is conducted while the acidic groups are in the form of free acid although the groups can be wholly or partially neutralised to form a water-soluble salt, for instance with alkali metal or amine or ammonia if desired.

The dispersing agent may be compounded with inorganic or organic particulate pigments in order to form a pigment paste which can be incorporated into an emulsion paint. The amount of dispersant agent is usually in the range 0.01 to 1% based on the weight of pigment.

The mole percent of the N-substituted acrylamide monomer, which monomer comprises at least one phosphonic or phosphinic acid or ester moiety component or components incorporated into the dispersant co-polymer ranges from about 0.1 to about 10 mole percent, preferably 0.1 to about 7 mole percent, and most preferably about 0.1 to about 5 mole percent based on the dispersant co-polymer.

The emulsion paint can be an anti-corrosive paint in which event the pigment will be a reactive pigment of the type utilised in anti-corrosive paints. For instance the pigment can be a zinc or aluminium oxide or borate or other salt or can be a calcium phosphate, for instance of the type present in Albritect™ anti-corrosive pigments, or an aluminium triphosphate pigment of the type present in "K-White"™ anti-corrosive pigments or a calcium strontium zinc phospho silicate pigment of the type present in Halox™ anti-corrosive pigments.

An advantage of the invention is that the dispersants give good results both in conventional paints and in anti-corrosive paints including a reactive pigment, and thus a manufacturer can use a single dispersant for all grades.

Additionally, the dispersants of the invention give good results when the pigment is non-reactive, for instance titanium dioxide, china clay and/or calcium carbonate. For instance the dispersants of the invention lead to good gloss values in conventional emulsion paints.

The paste or slurry can be formed in conventional manner, for instance by ball milling or otherwise blending and grinding the pigment, the dispersing agent and water, in appropriate amounts. The paste usually contains 50 to 90% pigment with the balance generally being water together optionally with minor conventional additives such as antifoam, thickener and/or glycol.

An emulsion paint can be formed in conventional manner by blending the pigment paste with a suitable binder latex. The latex can be, for instance, a vinyl acetate-vinyl ester of versatic acid latex, an ethylene vinyl acetate latex, a vinyl acetate-ethylene-vinyl chloride latex, an acrylic-ethylene-vinyl chloride latex, an acrylic latex or a styrene acrylic latex.

The amount of binder typically ranges from 20 to 80% and pigment 80 to 20% (dry weight). When the binder is a vinyl acetate or ethylene vinyl acetate latex it is often preferred for the paint to be formed from 20 to 40% dry weight binder and 60 to 80% pigment. Such paints may give a rather mat finish.

When higher quality, and usually higher gloss, paint films are required, the amount of binder is typically in the range 50 to 80% preferably 70 to 80%, with the amount of pigment being in the range 20 to 50% preferably 20 to 30% and with the binder generally being an acrylic or styrene acrylic latex.

These high binder paints tend to give coatings which are more water resistant and glossy and the use of the novel dispersant tends to increase still further the water resistance of the films formed from such paints.

A particular advantage of the dispersants of the invention is that they not only give improved water resistance but also give effective dispersing properties for a wide range of emulsion paints including matt and satin paints traditionally used on plaster or matt or gloss paints traditionally used on plaster or wood, as well as corrosion resistant gloss or other paints that may be used on metal. Accordingly, the invention provides a dispersant which has such wide ranging effectiveness that it is possible to utilise a single dispersant in substantially all grades of emulsion paint and to obtain thereby not only good water resistance but also satisfactory (for the particular emulsion paint concerned) covering power, stability and other properties.

Thus the invention includes the use by a manufacturer of the same dispersant in accordance with the invention, in anti-corrosive and conventional emulsions.

Water-borne for the purposes of the invention means coating, film or adhesive compositions wherein water is a substantial amount of the composition. Water may be a sole solvent and/or emulsifier. However, the compositions may also contain, in addition to water an organic solvent.

The water content of the compositions is governed substantially by the desired solids content of the composition. Preferred compositions contain about 5 to about 80% by weight of water and may be emulsions, dispersions or solutions.

The coatings, dispersants, films or adhesives may be applied to surfaces via any method known in the art.

For example, the coating materials can be applied to the substrate by the customary techniques, for example by spraying, dipping, spreading or electrodeposition. In many cases, a plurality of coats are applied.

The adhesion promoting or dispersing phosphonic or phosphinic acrylamide monomers or polymers formed from the phosphonic or phosphinic acrylamides monomers may be added to a base layer (primer) coating, since they are active in particular at the metal coating interface. However, they can also be added to the intermediate coat or topcoat, as well. Depending on whether the binder is a physically, chemically or oxidatively drying resin or a heat-curing or radiation-curing resin, the coating is cured at room temperature or by heating (stoving) or by irradiation.

The (meth)acrylamide phosphonic esters may be converted to the di or mono acids by standard synthetic means. For example, the phosphonate esters may be silylated with trimethylsilyl bromide followed by methanolysis to give the corresponding phosphonic acids in high yields.

Alternatively, (meth)acrylamide phosphonic acids may be prepared from appropriately unsaturated phosphonic acids via the Ritter synthesis with (meth)acrylonitrile procedure well known by those skilled in the art, such as that disclosed in U.S. Pat. No. 4,526,728

The following examples describe certain embodiments of this invention. It should be understood that numerous changes to the disclosed embodiments can be made in accordance with the disclosure herein without departing from the spirit or scope of the invention. These examples are therefore not meant to limit the scope of the invention. Rather, the scope of the invention is to be determined only by the appended claims and their equivalents.

In these examples all parts given are by weight unless otherwise indicated.

$^1$H and $^{31}$P NMR spectra were recorded on a 300 MHz Gemini Spectrometer at ambient temperature.

EXAMPLES

Phosphonate Containing (Meth)acrylamides

Example 1

Diethyl 4-(acrylamido)benzylphosphonate

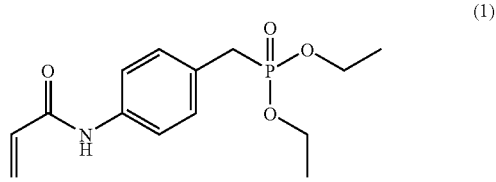

(1)

To a solution of diethyl 4-(amino)benzylphosphonate (2.02 g; 8.3 mmoles) and triethylamine (1.02 g; 9 mmoles) in toluene (7 ml) cooled to 0-5° C., is added dropwise a solution of acryloyl chloride (0.91 g of 95% purity; 10 mmoles) in toluene (2 ml) for 30 min. Thereafter, more toluene (5 ml) is poured into the flask and the mixture is stirred at room temperature for two more hours. The reaction is terminated by addition of water (10 ml). The organic phase is extracted with diethyl ether, dried over MgSO$_4$ and stripped of solvent under vacuum to afford a pale-yellow solid (2.22 g; yield 90%).

$^1$H NMR (CDCl$_3$, δ ppm) 1.26 (t, 6H, —CH$_2$—CH$_3$), 3.07 (s, 1H, —C$_6$H$_4$—CH$_2$—), 3.14 (s, 1H, —C$_6$H$_4$—CH$_2$—), 3.95-4.08 (m, 4H, —O—CH$_2$—), 5.68 (s, 1H, —CH=), 6.42 (d, 2H, —CH=), 7.16 (dd, 2H, —C$_6$H$_4$—), 7.53 (dd, 2H, —C$_6$H$_4$—), 7.78 (s, 1H, —CO—NH—). $^{31}$P NMR (CDCl$_3$, δ ppm) 27.01.

Example 2

Diethyl 4-(methacrylamido)benzylphosphonate

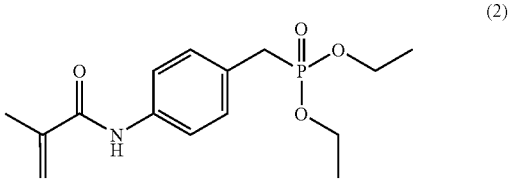

(2)

By the same procedure as described in example 1, diethyl 4-(amino)benzylphosphonate (1.94 g; 8 mmoles), triethylamine (0.87 g; 8.6 mmoles), and methacryloyl chloride (0.9 g; 8.6 mmoles) in toluene (9 ml) afford diethyl 4-(methacrylamido)benzylphosphonate as a slight yellow solid (2.3 g; yield 92%).

$^1$H NMR (CDCl$_3$, δ ppm) 1.25 (t, 6H, —CH$_2$—CH$_3$), 2.06 (s, 3H, CH$_3$—C=), 3.08 (s, 1H, —C$_6$H$_4$—CH$_2$—), 3.16 (s, 1H, —C$_6$H$_4$—CH$_2$—), 4.00 (m, 4H, —O—CH$_2$—), 5.45 (s, 1H, CH$_2$=), 5.81 (s, 1H, —CH$_2$=), 7.25 (dd, 2H, —C$_6$H$_4$—), 7.55 (dd, 2H, —C$_6$H$_4$—), 7.88 (s, 1H, —CO—NH—). $^{31}$P NMR (CDCl$_3$, δ ppm) 27.54.

Example 3

Tetraethyl 2,2'-iminobis(ethylphosphonate)

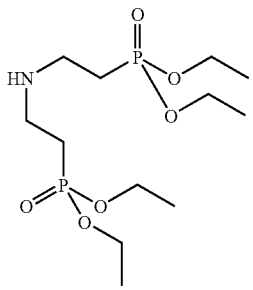 (3)

A solution of diethyl vinylphosphonate (10.52 g; 0.062 moles) in concentrated ammonia (14.4 g) is stirred for 2 days at room temperature. The reaction mixture is diluted with water (100 ml), extracted with dichloromethane (4×30 ml) and dried over MgSO$_4$. Stripping of the solvent in vacuo until constant weight affords a colorless liquid (8.36 g; yield 73%).

$^1$H NMR (CDCl$_3$, δ ppm) 1.27 (t, 12H, —CH$_2$—CH$_3$), 1.82 (s, 1H, —NH—), 1.88 (t, 2H, —CH$_2$—P—), 1.94 (t, 2H, —CH$_2$—P—), 2.85 (dt, 4H, —CH$_2$—N), 3.98-4-11 (m, 8H, —O—CH$_2$—). $^{31}$P NMR (CDCl$_3$, δ ppm) 31.4.

Example 4

Diethyl 2-aminoethylphosphonate

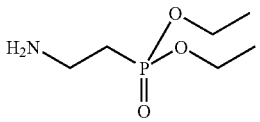 (4)

A mixture of diethyl cyanomethylphosphonate (17.7 g; 0.1 moles) in ethanol (70 ml) and aqueous HCl (40 ml of 10% HCl) over 10% Pd/C (1 g) is stirred in a pressure vessel at 60 psi. When the calculated amount of H$_2$ had been absorbed (about 26 hours), the catalyst is filtered off over Celite, washed with ethanol, and the filtrate is neutralized with NaHCO$_3$ and evaporated to dryness under vacuum. The residue is extracted with absolute ethanol (2×50 ml) and the clear extract is distilled at about 110° C. and 0.18 mbar to give a colorless liquid (11.4 g; yield 63%).

$^1$H NMR (CDCl$_3$, δ ppm) 1.31 (t, 6H, —CH$_2$—CH$_3$), 1.88-1.98 (dt, 2H, NH$_2$—CH$_2$—), 2.18 (s, 2H, broad, NH$_2$), 2.95-3.03 (dt, 2H, —CH$_2$—P—), 4.04-4.13 (m, 4H, —O—CH$_2$—). $^{31}$P NMR (CDCl$_3$, δ ppm) 30.97

Example 5

Diethyl[3-(N-phthalimido)]propylphosphonate

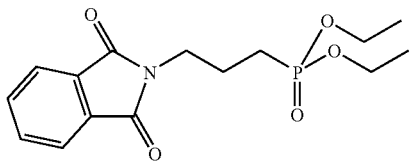 (5)

Potassium phthalimide (2.8 g; 15.1 mmoles) and diethyl 3-bromopropylphosphonate (3.92 g; 15.1 mmoles) are stirred vigorously at 98-100° C. for 2 hours. The mixture is cooled to room temperature, diluted with diethyl ether (15 ml) and filtered. Solvent stripping in vacuo affords a colorless liquid (4.52 g; yield 90%).

$^1$H NMR (CDCl$_3$, δ ppm) 1.29 (t, 6H, —CH$_2$—CH$_3$), 1.71-1.83 (m, 2H, —CH$_2$—P—), 1.89-2.04 (m, 2H, —CH$_2$—CH$_2$—CH$_2$—), 3.74 (t, 2H, —N—CH$_2$), 4.01-4.13 (m, 4H, —O—CH$_2$—), 7.71 (dd, 2H, —C$_6$H$_4$—), 7.83 (dd, 2H, —C$_6$H$_4$—). $^{31}$P NMR (CDCl$_3$, δ ppm) 31.95.

Example 6

Diethyl 3-aminopropylphosphonate

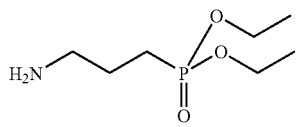 (6)

A mixture of diethyl[3-(N-phthalimido)]propylphosphonate (ex. 5) (3.72 g; 11.4 mmoles), absolute ethanol (46 ml) and hydrazine hydrate (0.78 ml of 98% purity; 15.7 mmoles) is stirred at reflux for 35 min. The mixture is filtered and the solvent is distilled under vacuo. The resulting oil is dissolved in CHCl$_3$ (10 ml) and is filtered again. Solvent removal in vacuo gives a colorless liquid (0.7 g; yield 30%). According to example 4, diethyl 3-aminopropylphosphonate (6) is also obtained from diethyl 2-cyanoethylphosphonate in an analogous fashion followed by vacuum distillation at about 115° C. and 0.18 mbar (yield 80%).

$^1$H NMR (CDCl$_3$, δ ppm) 1.28 (t, 6H, —CH$_2$—CH$_3$), 1.70-1.75 (m, 4H, —CH$_2$—P—), 2.01 (s, broad, NH$_2$—), 2.73 (t, 2H, NH$_2$—CH$_2$—), 4.02-4.09 (m, 4H, —O—CH$_2$—). $^{31}$P NMR (CDCl$_3$, δ ppm) 32.76.

Example 7

Tetraethyl 2,2'-N-acryloyliminobis(ethylphosphonate)

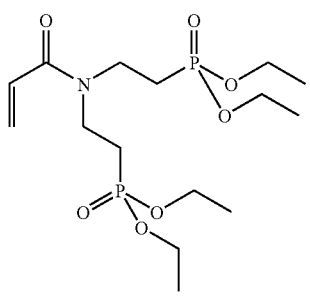 (7)

Acryloyl chloride (0.96 g; 10.6 mmoles) is added dropwise to a solution of tetraethyl 2,2'-iminobis(ethylphosphonate) from example 3 (3.35 g; 9.7 mmoles) in concentrated ammonia (28.8% aqueous ammonia; 1.32 g; 10.6 mmoles), cooled at −5° C. The reaction mixture is stirred for another 4 hours, quenched with water and extracted with dichloromethane. Filtration of the organic extracts followed by solvent evaporation in vacuo, gives a colorless liquid (2.9 g; yield 75%).

$^1$H NMR (CDCl$_3$, δ ppm) 1.31 (t, 12H, —CH$_2$—CH$_3$), 2.08 (m, 4H, —CH$_2$—P—), 3.60 (m, 4H, —N—CH$_2$—), 4.20 (m, 8H, —O—CH$_2$—), 5.70 (dd, 1H, —CH=), 6.46 (dd, 1H, —CH=), 6.55 (dd, 1H, —CH=). $^{31}$P NMR (CDCl$_3$, δ ppm) 27.99, 29.50.

Example 8

Tetraethyl 2,2'-N-methacryloyliminobis(ethylphosphonate)

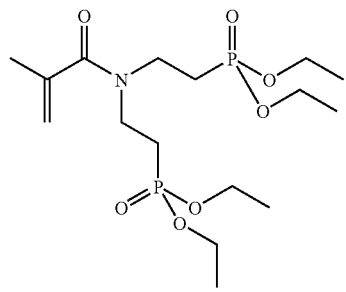

(8)

Methacryloyl chloride (1.7 g; 16.3 mmoles) is added dropwise to a solution of tetraethyl 2,2'-iminobis(ethylphosphonate) from example 3 (5.36 g; 15.5 mmoles) in concentrated ammonia (28.8% aqueous ammonia; 2.1 g; 15.9 mmoles), cooled at −5° C. The reaction mixture is stirred for another 4 hours, quenched with water and extracted with dichloromethane. Filtration of the organic extracts followed by solvent evaporation in vacuo, gives a colorless liquid (5.64 g; yield 91%).

$^1$H NMR (CDCl$_3$, δ ppm) 1.32 (t, 12H, —CH$_2$—CH$_3$), 1.95 (s, 3H, CH$_3$—C=), 2.08 (m, 4H, —CH$_2$—P—), 3.60 (m, 4H, —N—CH$_2$—), 4.20 (m, 8H, —O—CH$_2$—), 5.02 (dd, 1H, CH$_2$=), 5.19 (dd, 1H, CH$_2$=). $^{31}$P NMR (CDCl$_3$, δ ppm) 28.01, 29.39.

Examples 9-12 are prepared as in examples 1 and 2, where acryloyl chloride or methacryloyl chloride is reacted with diethyl 3-aminoethylphosphonate (as in example 4) or diethyl aminopropylphosphonate (as in example 6).

Example 9

Diethyl 3-(N-acrylamido)propylphosphonate

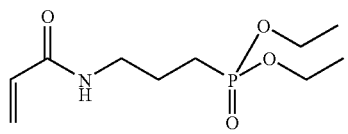

(9)

Example 10

Diethyl 3-(N-methacrylamido)propylphosphonate

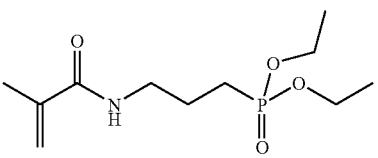

(10)

Example 11

Diethyl(N-acrylamido)ethylphosphonate

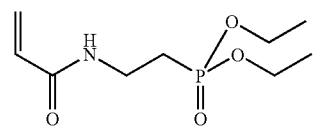

(11)

Example 12

Diethyl(N-methacrylamido)ethylphosphonate

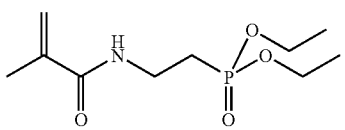

(12)

Example 13-18

Hydrolysis of examples 7-12 is carried out to form the corresponding diacids as exemplified in the procedure below.

Trimethylsilyl bromide (0.4 g; 2.6 mmoles) is added dropwise at room temperature to a solution of tetraethyl 2,2'-N-acryloyliminobis(ethylphosphonate) from example 7 (0.5 g; 1.24 mmoles) in dichloromethane (5 ml). The reaction mixture is refluxed under a nitrogen sparge for 4 hours, followed by evaporation of volatiles under reduced pressure. Methanol (5 ml) is added to the reaction crude and the mixture is stirred at room temperature for another 12 hours. Stripping of methanol under vacuum until constant weight affords the corresponding phosphonic acid.

Application Examples

Example 19

Polymerization of (meth)acrylamide phosphonic esters and acids (Examples 7-18)

The polymerization kinetics of (meth)acrylamide phosphonates from the examples above is evaluated by photoDSC. Polymerizations are done in bulk with neat monomer or polymerizable mixtures, under nitrogen with 2 mole % of Ciba's Irgacure 651 (2,2-dimethoxy-2-phenylacetophenone) and light intensity of 30 mW/cm$^2$ or 100 mW/cm$^2$. Polymerization occurrs with rates typical of acrylic functionalities, imparting excellent incorporation of the phosphorus-containing groups into corresponding co-polymers.

Example 20

Monomer Incorporation into Structural Adhesives

The adhesion promoting monomers made in the examples above are incorporated into a base formulation for structural adhesives. The monomers are mixed in the formulation at 1 and 3 parts by weight, and are applied to strips of steel, aluminum, and galvanized steel. The effectiveness of the adhesive is evaluated by measuring tensile strength after cure. Resin without metal adhesion promoter is used as reference.

Example 21

Copolymer Prepared from Butyl Methacrylate and Phosphonate(Meth)acrylamides In a 100-mL flask equipped with a magnetic stirrer and condenser under nitrogen, a polymerizable phosphonate acrylamide (examples 7-18) is combined with butyl methacrylate in toluene, in a molar ratio of 1:30 (phosphonate:butyl methacrylate). The mixture is degassed and placed in a constant-temperature bath at 70° C. 2,2'-Azobis(isobutyronitrile) is added and the mixture is stirred until copolymerization is complete. The copolymer is precipitated and dried, and used in subsequent formulations as an adhesion enhancer.

Example 22

Coating solutions of 20% by weight of solids are made up incorporating various percentages (about 5 weight % to about 50 weight %) of the copolymers prepared in example 21. Solutions are applied to galvanized steel plates using a bar-coater. Solvent and water are evaporated in an aerated oven. The adhesion of the coating to the steel plates is good.

Example 23

UV-Curable Coating

A base UV-curable formulation containing co-monomers, oligomer and photoinitiator is made and then 1 and 3 parts by weight of the phosphorus-containing (meth)acrylamides from the examples above are added based on total solids. The formulations are cured using two 300 watts per inch mercury vapor lamps measuring 750 mJ/cm² energy for a 5.0-6.0 μm thick coating. Adhesion of the coating to steel, aluminum and glass is good.

We claim:

1. An adhesive, coating or film composition applied to a surface wherein, the composition comprises a polymer formed from at least one N-substituted acrylamide monomer represented by at least one of the formulae (I), (II), (III) or (IV)

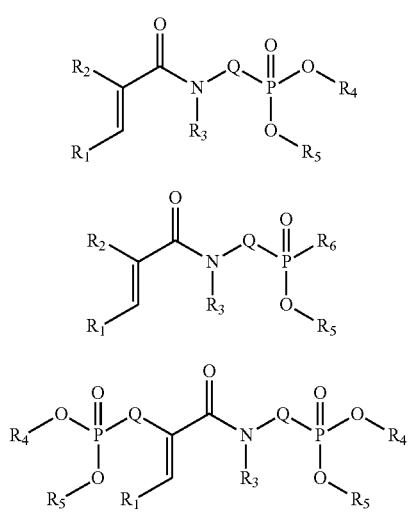

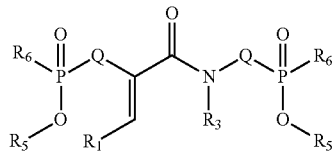

wherein

Q is a divalent linking radical selected from the group consisting of one or more of a $C_6$-$C_{12}$ arylene and aralkylene;

wherein the linking radical is unsubstituted or substituted by one or more $C_1$-$C_4$ alkyl, $C_1$-$C_4$ haloalkyl, halogen, —P(O)(OR$_4$)(OR$_5$), -Q'-P(O)(OR$_4$)(OR$_5$), —P(O)(OR$_4$)(R$_6$), -Q'-P(O)(OR$_4$)(R$_6$), hydroxy or $C_1$-$C_4$ alkoxy;

or

Q is a $C_2$-$C_{12}$ alkylene interrupted by one or more —O—, —S—, —NR$_4$—, —O(CO)—, —S(CO)—, —OC(O)O—, —NR$_4$—C(O)—O—, —C(O)— or —NR$_4$(CO)—;

$R_1$ and $R_2$ are independently hydrogen, branched or unbranched $C_1$-$C_4$ alkyl;

$R_3$ is hydrogen or $C_1$-$C_4$ alkyl, -Q"-P(O)(OR$_4$)(OR$_5$) or -Q"-P(O)(OR$_4$)(R$_6$);

Q' and Q" are the same or different and are at least a divalent radical selected from the group consisting of one or more of a $C_1$-$C_{18}$ alkylene, $C_6$-$C_{12}$ arylene, and aralkylene;

wherein the divalent radical is unsubstituted or substituted by one or more $C_1$-$C_4$ alkyl, $C_1$-$C_4$ haloalkyl, halogen, —P(O)(OR$_4$)(OR$_5$), —P(O)(OR$_4$)(R$_6$), hydroxy or $C_1$-$C_4$ alkoxy;

or

Q' and Q" are a $C_2$-$C_{12}$ alkylene interrupted by one or more —O—, —S—, —NR$_4$—, —O(CO)—, —S(CO)—, —OC(O)O—, —NR$_4$—C(O)—O—, —C(O)— or —NR$_4$(CO)—;

$R_4$ and $R_5$ are independently H, $C_1$-$C_4$ alkyl wherein the $C_1$-$C_4$ alkyl is branched or unbranched, unsubstituted or substituted by $C_1$-$C_4$ alkyl, $C_6$-$C_{12}$ aryl or halogen; and $R_6$ is branched or unbranched $C_1$-$C_8$ alkyl, aryl, aralkyl, wherein the $C_1$-$C_8$ alkyl, aryl, aralkyl is unsubstituted or substituted by one or more $C_1$-$C_4$ alkyl, $C_1$-$C_4$ haloalkyl or halogen and the surface is selected from the group consisting of a metallic pigment particle, metal, glass, ceramic fiber, sheet metal and metal alloys, wherein at least one of $R_4$ or $R_5$ of formulae (I) or (III) is hydrogen.

2. A composition according to claim 1, wherein the composition is water-borne.

3. A composition according to claim 1, wherein the composition is cured by radiation.

4. A composition according to claim 1, wherein $R_4$ and $R_5$ are both hydrogen.

5. A composition according to claim 1, wherein $R_5$ of formulae (II) or (IV) is hydrogen.

6. A composition according to claim 1, wherein the polymer is a copolymer additionally formed from a second unsaturated monomer.

7. A composition according to claim 1 further containing a metallic pigment.

* * * * *